United States Patent [19]

Inoue et al.

[11] 4,376,681

[45] Mar. 15, 1983

[54] METHOD OF MEASURING CARBON DIOXIDE IN A LIQUID OR GAS

[75] Inventors: Tomoaki Inoue, Machida; Yoichi Ishikawa; Mitsunori Kaneko, both of Tokyo, all of Japan

[73] Assignee: Oriental Yeast Co., Ltd., Tokyo, Japan

[21] Appl. No.: 170,919

[22] Filed: Jul. 21, 1980

[30] Foreign Application Priority Data

Jan. 8, 1979 [JP] Japan ............................. 54-1082

[51] Int. Cl.³ .................. G01N 27/56; A61L 2/06
[52] U.S. Cl. ...................... 204/1 T; 204/195 P; 422/26
[58] Field of Search ............ 204/1 K, 195 P; 128/635; 422/26

[56] References Cited

U.S. PATENT DOCUMENTS

| | | | |
|---|---|---|---|
| 3,575,836 | 4/1971 | Sternberg | 204/195 P |
| 3,649,505 | 3/1972 | Strickler et al. | 204/195 P |
| 3,764,504 | 10/1973 | Arff et al. | 204/195 P |
| 3,853,731 | 12/1974 | Gray et al. | 204/195 G |
| 4,012,308 | 3/1977 | Jerrold-Jones et al. | 204/195 F |
| 4,078,981 | 3/1978 | Neti et al. | 204/195 P |

OTHER PUBLICATIONS

John W. Severinghaus et al., J. Appl. Physiology, vol. 13, No. 3, pp. 515–520, (1958).
Richard W. Stow, Arch. Phys. Med. Rehabil., 38, pp. 646–650, (1957).

*Primary Examiner*—G. L. Kaplan
*Attorney, Agent, or Firm*—Stevens, Davis, Miller & Mosher

[57] ABSTRACT

A carbon dioxide sensor for measuring dissolved carbon dioxide or carbon dioxide in gas is sterilizable with steam under pressure at a temperature of 120–130 degrees Celsius. The sensor comprises an outer tube having on its one end a gas-permeable membrane and a pH electrode disposed in the outer tube and supporting a spacer of poor hydrophobicity so as to be positioned between the distal end of the electrode and the membrane. For measurement of carbon dioxide, a liquid containing sodium bicarbonate is poured into the outer tube to form a layer of electrolyte at the spacer, and the outer tube is mounted on a fermentor. The pH electrode can be removed from the outer tube which is attached to the fermentor, and a membrane protecting rod can be inserted into the outer tube for sterilization of the membrane. The gas-permeable membrane can easily be replaced.

1 Claim, 4 Drawing Figures

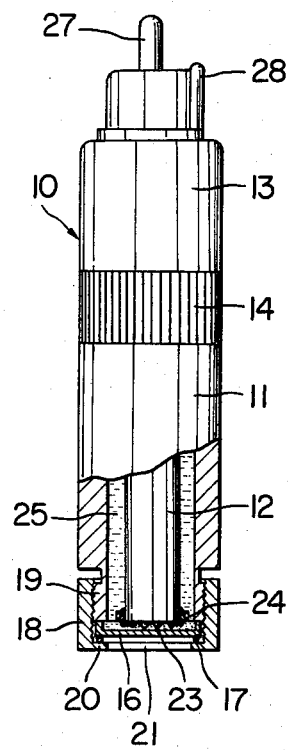
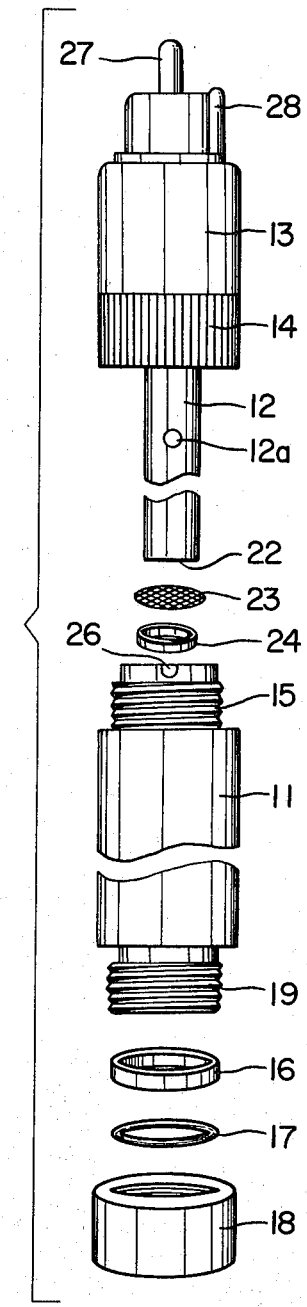

FIG. 3
FIG. 4
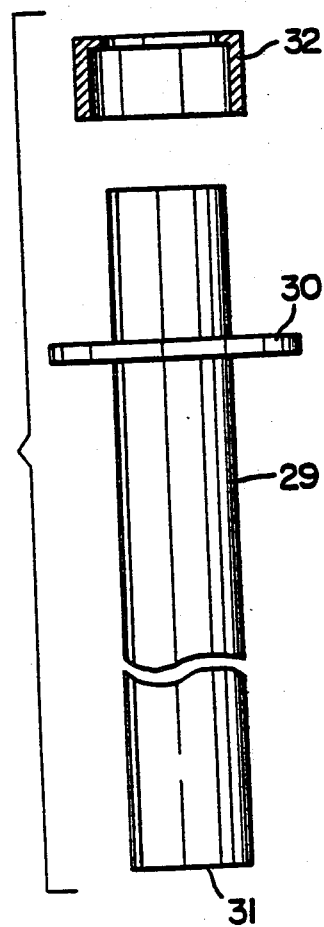
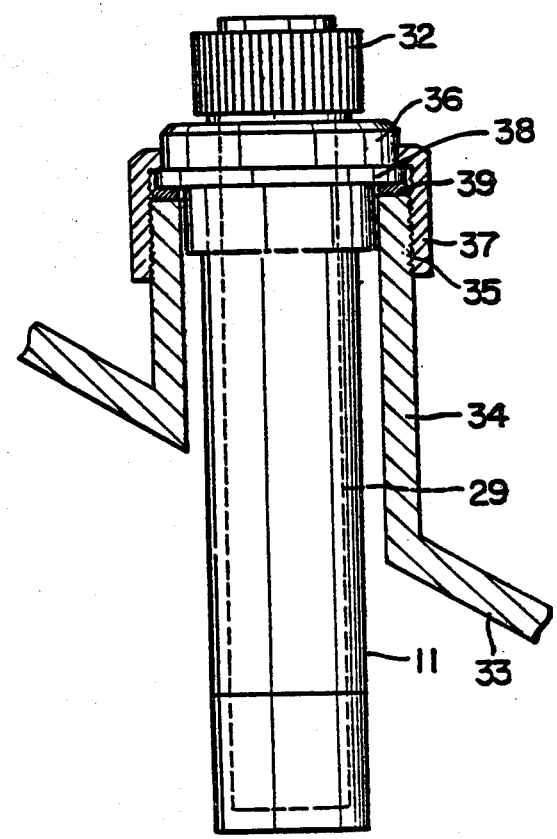

METHOD OF MEASURING CARBON DIOXIDE IN A LIQUID OR GAS

BACKGROUND OF THE INVENTION

1. Field of the Invention

The present invention relates to a carbon dioxide concentration sensor that is sterilizable with steam under pressure at a temperature ranging from 120 to 130 degrees Celsius, and a method of using such sensor.

2. Prior Art

The importance of measurement of dissolved oxygen was suggested by Hixon, Gaden and Finn in the 1950s in the fermentation engineering field. As a result, a dissolved oxygen sensor was developed and has been widely used which can withstand sterilization with steam under pressure. It has recently been found that control of a fermentation process can advantageously be effected by measuring carbon dioxide as well as dissolved oxygen in the fermentation broth or gas discharged from the fermentor.

In the medical field, a sensor for electrochemically measuring the concentration of carbon dioxide in blood was already developed by Stow [Arch. Phys. Med. Rehabil., 38,646 (1957)] and Severinghaus [(J. Appl. Physiol., 13,515 (1958): Ann. N.Y. Acad. Sci., 148,115 (1965)], and has been in widespread use as a $P_{CO_2}$ probe. Such sensor comprises a rod-like combination-type pH electrode including a reference electrode therein and covered by a membrane which is highly permeable to carbon dioxide gas, there being a thin layer of aqueous solution containing alkali bicarbonate interposed between the membrane and a glass surface serving as a sensing element of the pH electrode. When the sensor is placed in a liquid or gas containing carbon dioxide, $CO_2$ gas permeates the membrane and gets disolved in an electrolyte solution in the sensor, wherein part of the $CO_2$ gas produces carbonic acid and bicarbonic acid, thereby changing the value of pH of the electrolyte solution.

It has already been attempted to use this type of sensor in the fermentation engineering field. However, the coventional $P_{CO_2}$ sensor has not found wide usage because when it is sterilized with steam under pressure, the electrolyte solution boils, the membrane is damaged, and the pH electrode loses its sensitivity due to heat.

The present inventors have provided a sensor and a method of using the same which are suitable especially for use in the fermentation engineering field, based on improvement of a sensor of the type proposed by Stow and Severinghaus.

SUMMARY OF THE INVENTION

A carbon dioxide concentration sensor, which is sterilizable with steam under pressure, comprises a combination-type pH glass electrode disposed in an outer tube supporting on its distal end a gas-permeable membrane. The pH glass electrode has on its flat end a glass surface wrapped up by a spacer of gauze disposed adjacent to the membrane. When a solution of electrolyte is poured into the outer tube, a thin layer of electrolyte is formed between the tip of the pH glass electrode and the membrane on the outer tube. For sterilization of the membrane, the pH glass electrode can be replaced with a membrane protecting rod having substantially the same outside dimension as that of the pH glass electrode.

An object of the present invention is to provide a carbon dioxide sensor which is sterilized with steam under pressure while being mounted on a fermentor.

Another object of the present invention is to provide a method of measuring the concentration of $CO_2$ in a fermentor with such a sensor mounted thereon.

Still another object of the present invention is to improve fermentation process control with such a sensor.

Still another object of the present invention is to provide a simple and stabilized $CO_2$ meter that can be used in both gas and liquid.

These and other objects and advantages will become apparent from the detailed description with reference to the accompanying drawings.

BRIEF DESCRIPTION OF THE DRAWINGS

FIG. 1 is a front elevational view, with parts in cross section, of a carbon dioxide sensor according to the present invention;

FIG. 2 is an exploded view of the carbon dioxide sensor shown in FIG. 1;

FIG. 3 is a front elevational view of a membrane protecting rod; and

FIG. 4 is a cross-sectional view of the carbon dioxide sensor mounted on a fermentor with a pH electrode being replaced with the membrane protecting rod for sterilization.

DETAILED DESCRIPTION

As shown in FIGS. 1 and 2, a carbon dioxide sensor 10 constructed according to the present invention comprises an outer sleeve or tube 11 of stainless steel, and a pH glass electrode 12 of glass disposed concentrically within the outer tube 11 and mounted on an upper cap 13 which is coaxially attached to the outer tube 11 by a nut 14 threaded over an externally threaded portion 15 of the outer tube 11. The pH glass electrode 12 has an electrolyte filling port 12a for a reference electrode (not shown). A gas-permeable membrane 16, with an O-ring attached, of silicone rubber having a thickness on the order of $100\mu$ is axially held against the outer tube 11 by a cap nut 18 threaded over an externally threaded portion 19 of the outer tube 11 with an O-ring 17 of polytetrafluoroethylene disposed between the membrane 16 and an annular retainer flange 20 of the cap nut 18. The cap nut 18 has an opening 21 through which bubbles can escape.

The pH glass electrode 12 has on its flat end or distal end a sensor membrane 22 of glass wrapped up by a mesh spacer 23 of gauze which has a thickness of approximately 0.15 mm and which is retained on the pH glass electrode 12 by a spacer band 24. The spacer 23 protects the sensor membrane 22 against being damaged when the pH glass electrode 12 is assembled into or disassembled from the outer tube 11, and provides a layer of electrolyte between the membrane 16 and the pH glass electrode end surface 22, which layer of electrolyte is sufficient in amount for keeping the performance of the sensor 10 in the best condition. An electrolyte 25 (FIG. 1) is contained in the outer tube 11 in which the pH glass electrode 12 is mounted. The externally threaded portion 15 of the outer tube 11 has a slot 26 which fits over a projection (not shown) on the cap 13 for preventing relative rotation of the cap 13 and outer tube 11. The cap 13 supports thereon a pair of terminals 27, 28 connected respectively to the pH glass electrode 12 and the reference electrode.

A membrane protecting rod 29 of stainless steel illustrated in FIG. 3 replaces the pH glass electrode 12 when the membrane 16 is to be sterilized with steam, as described later on. The membrane protecting rod 29 has a flange 30 and a lower end 31 against which the membrane 16 is to be held. A cap nut 32 secures the membrane protecting rod 29 to the outer tube 11.

FIG. 1 shows the assembled sensor 10 ready for measurement of carbon dioxide, $CO_2$. The sensor 10 is assembled as follows: The spacer 23 is first attached to the distal end of the pH electrode 12 by the spacer band 24. The O-ring 17 is placed in the cap nut 18 against the retainer flange 20 and then the membrane 16 is put into the cap nut 18 with the attached O-ring above. The cap nut 18 with the O-ring 17 and the membrane 16 assembled therein is then threaded over the externally threaded portion 19 of the outer tube 11. The electrolyte 25, which contains $NaHCO_3$ of a concentration on the order of 10 mM and NaCl of a concentration on the order of 1 M, is poured into the outer tube 11 with its bottom closed by the membrane 16. The pH glass electrode 12 is then inserted slowly into the outer tube 11 all the way down from above, and thereafter the nut 14 is tightened on the externally threaded portion 15 of the outer tube 11 to connect the cap 13, and hence the pH glass electrode 12, with the outer tube 11. The sensor 10 is thus put together as illustrated in FIG. 1.

Since the pH glass electrode 12 is held non-rotatable with respect to the outer tube 11 by the slot 26 and its companion projection on the cap 13, the membrane 16 is prevented from frictional damages which would otherwise result from relative rotation between the pH glass electrode 12 and the outer tube 11.

As shown in FIG. 4, the outer tube 11 with the pH glass electrode 12 and the cap 13 being replaced with the membrane protecting rod 29 inserted therein and the membrane 16 supported thereon, is placed in an access pipe 34 on a fermentor wall 33 for steam sterilization of the membrane 16. While the outer tube 11 may be secured to the access pipe 34 by a rubber stud (not shown), the outer tube 11 may have a flange 36 including a shoulder 38 which can be held against the access pipe 34 with an O-ring 39 therebetween by a nut 37 threaded over an externally threaded portion 35 of the access pipe 34.

For measurement of concentration of carbon dioxide, the output of the sensor 10 should first be calibrated by a sensitivity regulator or a calibration curve prepared when two kinds of reference gas (for example, gases of high and low concentrations such as about 9–10V% and 1V% within a measurable range) are introduced into a fermentor. When no reference gas is readily available, a reference liquid containing $CO_2$ of 0.1 M may be prepared by adding acid to an aqueous solution of $NaCHO_3$ of a known concentration such as of 0.1 M.

Where the sensor is to be used with a relatively large fermentor, the sensor should be calibrated on a small container that is utilized for calibration of the sensor only.

Since the value of pH (mV) and the logarithmic value of a $CO_2$ concentration are in linear relation, the $CO_2$ concentration becomes difficult to read as it goes higher. Accordingly, it is desirable to use an amplifier circuit for indicating the $CO_2$ concentration on a uniform scale based on antilog.

The sensor according to the present invention can measure $CO_2$ having concentrations of 0–0.2V%, 0.2–1V%, 0–10V% and dissolved carbon dioxide having corresponding concentrations with an error of ±3% with respect to the full scale, with the result that the sensor can reliably be indicative of the manner in which carbon dioxide is generated during incubation of microorganisms.

The sensor has been sterilized in an autoclave twenty times each for 15 minutes at a temperature of 120 degrees Celsius. No change in its responsiveness has resulted. The sensor has proved 90% responsive in an interval of 45–60 seconds.

According to the present invention, the concentration of $CO_2$ in liquid or gas can automatically and continuously be measured simply by measuring an output in terms of mV from a sensor that is of a relatively simple structure in which a pH electrode is housed. The sensor is sterillized with steam under pressure with the pH glass electrode being removed which is susceptible to heat. Therefore, the pH glass electrode can be used for a prolonged period of time, which is highly economical.

During sterilization, the gas permeable membrane 16 can be protected by the membrane protecting rod 29 against damages under pressure. When the membrane became dirty or damaged, it can readily be replaced with a new one.

With the spacer 23 of gauze being mounted on the flat end of the electrode, a desired layer of electrolyte can be provided between the membrane and the flat end of the electrode for satisfactory operation of the sensor. The spacer also serves to protect the flat end of the pH glass electrode when the latter is to be assembled or disassembled. The membrane 16 can be replaced with a new one simply by removing the lower cap 18.

Although a certain preferred embodiment has been shown and described in detail, it should be understood that various changes and modifications may be made therein without departing from the scope of the appended claims.

What is claimed is:

1. A method of measuring carbon dioxide concentration in liquid or gas, comprising the steps of: inserting a membrane into a lower cap and mounting said lower cap on an outer tube to close a lower end of said outer tube with said lower cap; inserting a membrane protecting rod into said outer tube and securing said rod to said outer tube with an upper cap; placing said outer tube in a hole in a cover or sidewall of a vessel containing the material to be tested; sterilizing said outer tube with steam and then cooling the same; pulling out only said membrane protecting rod; introducing electrolyte into said outer tube; inserting a pH glass electrode into said outer tube; connecting said pH glass electrode to an indicator; and detecting a change in pH of said electrolyte which occurs when carbon dioxide gas in said vessel permeates said membrane and is dissolved into said electrolyte wherein the carbon dioxide is formed into carbonic acid.

* * * * *

UNITED STATES PATENT AND TRADEMARK OFFICE
CERTIFICATE OF CORRECTION

PATENT NO. : 4,376,681

DATED : March 15, 1983

INVENTOR(S) : Tomoaki Inoue et al.

It is certified that error appears in the above-identified patent and that said Letters Patent are hereby corrected as shown below:

Column 3, lines 54-55: "$NaCHO_3$" should be "$NaHCO_3$".

Column 4, line 21: "sterillized" should be "sterilized".

Column 4, line 28: "became" should be "becomes".

Signed and Sealed this

Twenty-first Day of June 1983

[SEAL]

Attest:

DONALD J. QUIGG

Attesting Officer    Acting Commissioner of Patents and Trademarks